United States Patent [19]

Fletcher, III et al.

[11] Patent Number: 5,286,358

[45] Date of Patent: Feb. 15, 1994

[54] METHOD OF ANALYZING THE COMPLEXING POWER OF A PICKLING LIQUOR

[75] Inventors: Kenneth S. Fletcher, III, Rehoboth; Jane K. Burdick, North Attleboro, both of Mass.

[73] Assignee: The Foxboro Company, Foxboro, Mass.

[21] Appl. No.: 738,872

[22] Filed: Aug. 1, 1991

[51] Int. Cl.$^5$ .................. C23G 1/02; G01N 33/00
[52] U.S. Cl. .................. 204/153.13; 134/2; 134/3; 134/41; 436/101; 436/125; 204/405
[58] Field of Search .................. 436/101, 125; 134/2, 134/3, 41; 204/153.13

[56] References Cited

U.S. PATENT DOCUMENTS

| | | | |
|---|---|---|---|
| 3,027,240 | 3/1962 | Bartell et al. | 436/100 |
| 3,393,980 | 7/1968 | Johnson et al. | 436/125 |
| 3,542,518 | 11/1970 | Morrow | 436/101 X |
| 5,154,774 | 10/1992 | Bousquet et al. | 134/3 |

OTHER PUBLICATIONS

McKaveney, J. P., Analytical Chemistry, vol. 40, No. 8, pp. 1276-1279 (Jul. 1968).

Primary Examiner—T. Tung
Assistant Examiner—William T. Leader
Attorney, Agent, or Firm—Lahive & Cockfield

[57] ABSTRACT

A method is provided for accurately determining the complexing capacity (or free HF concentration) of a pickling liquor. A sample of pickling liquor is obtained and an excess of ferric ion is added thereto to complex with all of the free HF in the sample. A back titration is performed to determine the residual free ferric ion. The difference between the amount of ferric ion added and that found by the titration is related to the free HF in the original sample.

The method is useful in conjunction with an automated, on-line system which periodically monitors a pickling bath and makes any necessary adjustments thereto.

11 Claims, 3 Drawing Sheets

METHOD OF ANALYZING THE COMPLEXING POWER OF A PICKLING LIQUOR

BACKGROUND OF THE INVENTION

This invention relates to a method and system for determining the effective ferric ion-complexing capacity of a hydrofluoric acid-containing cleaning liquid. The invention is particularly well adapted for use with mixed acid (hydrofluoric and nitric acids) pickling liquors, such as those used in steel processing.

Various grades of steel, including stainless steel, are cleaned during processing with a pickling liquor to remove oxides and scale from the surface of the metal. Pickling liquors typically comprise a concentrated, mixed acid solution of hydrofluoric acid (HF) and nitric acid ($HNO_3$).

During a pickling process nitric acid, a strong oxidizer, is used to dissolve oxides and scale from the metal surface. These are primarily oxides of iron in stainless steel, but are also oxides of chromium, nickel and minor amounts of other metals. Fluoride, in the form of hydrogen fluoride, is added to the bath to complex these metal ions as they are dissolved. In the absence of fluorides, a passive layer would form on the steel due to hydrolysis, and pickling would quickly cease. Hydrogen fluoride is able to hold these metals in solution through the formation of metal complexes represented by the general formulas $H_3MF_6$ and $H_2MF_5$, where M is a metal such as Fe, Ni or Cr. In addition, siliceous scale, containing non-metallic silica, is also cleaned through the formation of soluble silicon fluoride complexes.

Optimum concentration levels of acids and of fluoride, as HF, in a pickling liquor are to be maintained to ensure proper and efficient pickling. Thus, frequent monitoring of the pickling bath is desirable. However, there is no standard analytical method for monitoring the condition of a pickling bath. Indeed, controversy exists as to whether the proper species to analyze is free fluoride ion, total fluoride, hydrogen fluoride concentration, or combinations thereof.

Accurate analysis of the pickling bath is difficult because free fluoride ion ($F^-$) is not present in a measurable quantity due to the highly acidic nature of the bath. As pickling progresses, HF, the active complexer, is consumed with the formation of complexes. Analytical methods which seek to measure the concentration of fluoride ion require an upward adjustment of the pH of the sample. However, such techniques foster inaccurate results as the pH adjustment disturbs the chemical equilibrium relationships that exist in the bath. For example, if the pH is adjusted to 4, HF dissociates to $F^-$, and complexed metal, as $H_3MF_6$, is converted to hydrolytic compounds such as $M(OH)_x$, while HF is liberated. Analysis of HF under these conditions thus gives inaccurate results because the pH change causes the sample being analyzed to contain more HF than the actual pickling bath. Data obtained through such techniques are thus not relevant to the actual pickling liquor. Moreover, such techniques use "grab samples", which are pickling liquor samples removed from the pickling bath and analyzed off-line, often at a remote location. These methods do not provide "real time" information as desired to assess the ever changing conditions of an industrial pickling line.

Accordingly, there is a need for a real-time method of analyzing the condition of a mixed acid liquid, such as a pickling bath, to provide reliable and accurate information on the ability of the bath to continue a pickling process at an acceptable rate.

It is thus an object of the invention to provide an improved method for determining the iron-complexing power of a pickling bath. Another object of the invention is to provide an analytical method for performing an analysis of the iron-complexing power of a pickling bath which does not require a significant change in the pH of the sample. It is also an object of the invention to perform the analysis in an on-line manner, and to obtain data in essentially real-time. A further object of the invention is to provide a system for performing on-line, automated measurements of the iron-complexing power of a pickling liquor. Other objects of the invention will be apparent from the disclosure which follows.

SUMMARY OF THE INVENTION

The present invention features an on-line method for determining the complexing power of a mixed acid ($HF/HNO_3$) liquid, such as a pickling liquor, used to clean various types of steel. The complexing power of the bath is effectively a measure of the relative amount of available hydrofluoric acid present in the bath at a given time. The relative amount of available hydrofluoric acid provides an indication of the amount of fluoride available to complex with ferric ions. This value may be expressed relative to the amount of HF originally present in the bath.

As noted above, the oxidizing action of nitric acid in a pickling bath liberates scale, oxides and metal ions, including ferric ions. As the metal ions are released, they combine with HF, causing a decrease in the HF concentration and the efficiency of the bath. A determination of the complexing power (or available HF) provides a direct indication of the ability of the bath to continue the pickling process.

The method of the invention may be performed according to the following general steps. First, a sample of the pickling liquor is obtained and, optionally, diluted with a non-critical volume of distilled or deionized water. A known stoichiometric excess of ferric ion ($Fe^{+3}$), in a nitric acid solution, is added to the sample. The added ferric ion complexes with all of the HF not already complexed by metals in the bath. A back titration is then performed to determine the residual free ferric ion. The difference between the amount of ferric ion added and that found by the titration is related to the complexing capacity of HF in the original sample.

The back titration uses potassium iodide (KI) and sodium thiosulfate ($Na_2S_2O_3$). A potassium iodide reducing agent is added to the sample and reacts with uncomplexed, excess ferric ion to form an equivalent amount of iodine. Iodine is conveniently measured using a sodium thiosulfate titrant. The amount of sodium thiosulfate required to titrate the iodine can be shown to be stoichiometrically equivalent to the $Fe^{+3}$ not complexed by the fluoride in the sample. The difference between the amount of $Fe^{+3}$ added and that measured in this way is related to the available HF, and thereby to the complexing power, of the liquor by the relationship:

$$[HF]_{free} = k([Fe^{+3}]_{added} - [Fe^{+3}]_{found}),$$

where k is a dimensionless proportionality constant related to stoichiometry of the iron-fluoride complex formed. The progress of the iodometric titration may be followed, and the end point determined, by monitoring the oxidation-reduction potential of the solution with suitable Redox (ORP) and reference electrodes or through colorimetric methods.

The foregoing method can be practiced using a monitoring apparatus that is part of the pickling bath line. This practice of the invention can make periodic measurements of the actual pickling bath, and can obtain results relevant to the current condition of the bath in real time, i.e., in less than about ten minutes.

DETAILED DESCRIPTION OF THE INVENTION

The method of the invention can be used in either an on-line or an off-line manner to determine the complexing power of pickling liquor. An "on-line" analysis of a pickling liquor typically is one which is performed as part of any industrial pickling process line, such as that shown in FIG. 1. Preferably an on-line analysis is automated and provides data in real time, i.e., within about ten minutes of the time a sample is taken, for use with a control system. An "off-line" analysis is one in which a sample from a pickling line is analyzed independently of the current operation of the pickling line and hence without the objective of adjusting the current operation of the line. The off-line analysis typically does not provide data in real time. A preferred embodiment of the invention involves an on-line analysis of pickling liquor.

Pickling liquors, as noted above, are used to clean the surfaces of steels, particularly stainless steel, with one or more concentrated acids. A common pickling liquor is a mixture of concentrated hydrofluoric acid (HF) and concentrated nitric acid (HNO$_3$) in an aqueous solution. Typically, the hydrofluoric acid is present at 0.25 to 5.0 g HF/100 ml of the liquor, and the nitric acid is present at 5.0 to 15.0 g HNO$_3$/100 ml of liquor. Depending upon the stage of the pickling process, the concentration of iron present in the pickling liquor ranges from 0 to 8%.

Hydrogen fluoride is provided to complex Fe$^{+3}$ as it is formed during pickling so as to maintain efficiency of the pickling process. Thus, the concentration of HF must be maintained so that fluoride is available to complex with Fe$^{+3}$ ions, and to enable HNO$_3$ to oxidize and remove scale from the surfaces being treated. It follows that a pickling liquor having a high concentration of HF will indicate a low concentration of Fe$^{+3}$ ions, and visa versa. Accordingly, continuous monitoring of the pickling liquor is important in order to ensure a proper concentration of acids.

Figure 1:
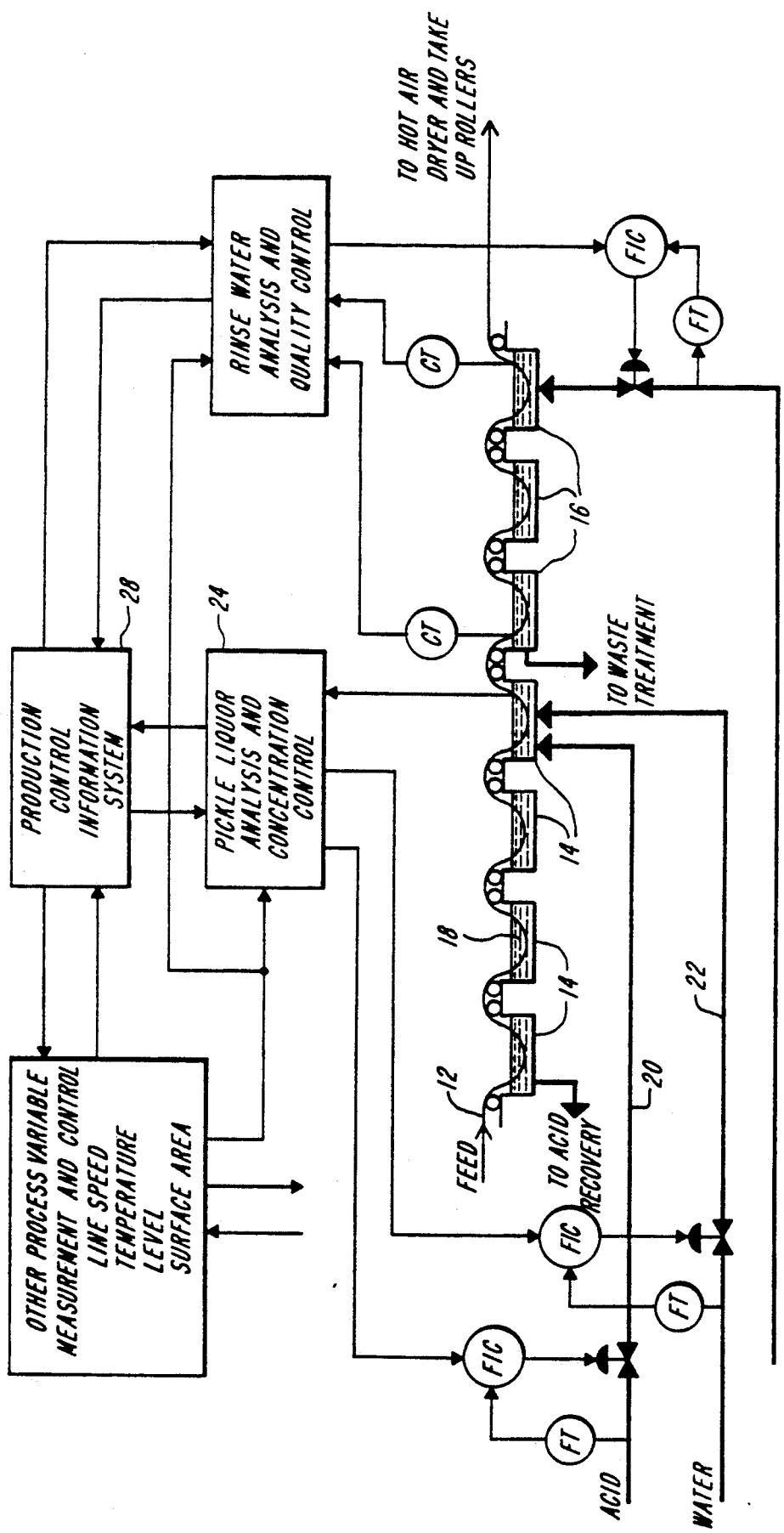
FIG. 1 is a schematic illustration of an industrial pickling line with which the method of the invention can be used.

FIG. 1 illustrates a typical industrial-type pickling line 10 having a feed line 12 for transporting metals such as steel (not shown) through pickling tanks 14, and rinse tanks 16. Pickling tanks 14 contain a pickling liquor 18 of the type described above. The pickling line also includes acid input line 20 and water input line 22.

In a preferred embodiment of the invention, the pickling line 10 also includes a pickling liquor analysis and monitoring unit 24. This monitoring unit 24 automatically samples the pickling liquors at predetermined time intervals and, according to the method of the invention, conducts measurements, typically by titration, to assess the effective complexing capacity (or available HF concentration) of a given pickling liquor sample. Information derived from the monitoring unit 24 can be evaluated by a production control station 28 which signals various controllers to make any necessary adjustments in the pickling system, including concentration of acids in the pickling liquor. The production control station 28 can employ known constructions and operate in a manner known in the art.

A preferred monitoring unit 24 is the FPA 300 Series Process Titrator, available from The Foxboro Company, East Bridgewater, Mass. This titrator includes a sampling loop which automatically gathers a sample, a reaction vessel, as well as the hardware and software necessary to add reagents and conduct titration to assess the complexing power of pickling liquor samples according to the method of the present invention. The design details of such a monitoring unit may vary depending upon the requirements of a given application. Given the method of the invention, one skilled in the art will be able to arrive at a suitable design.

Figure 3:
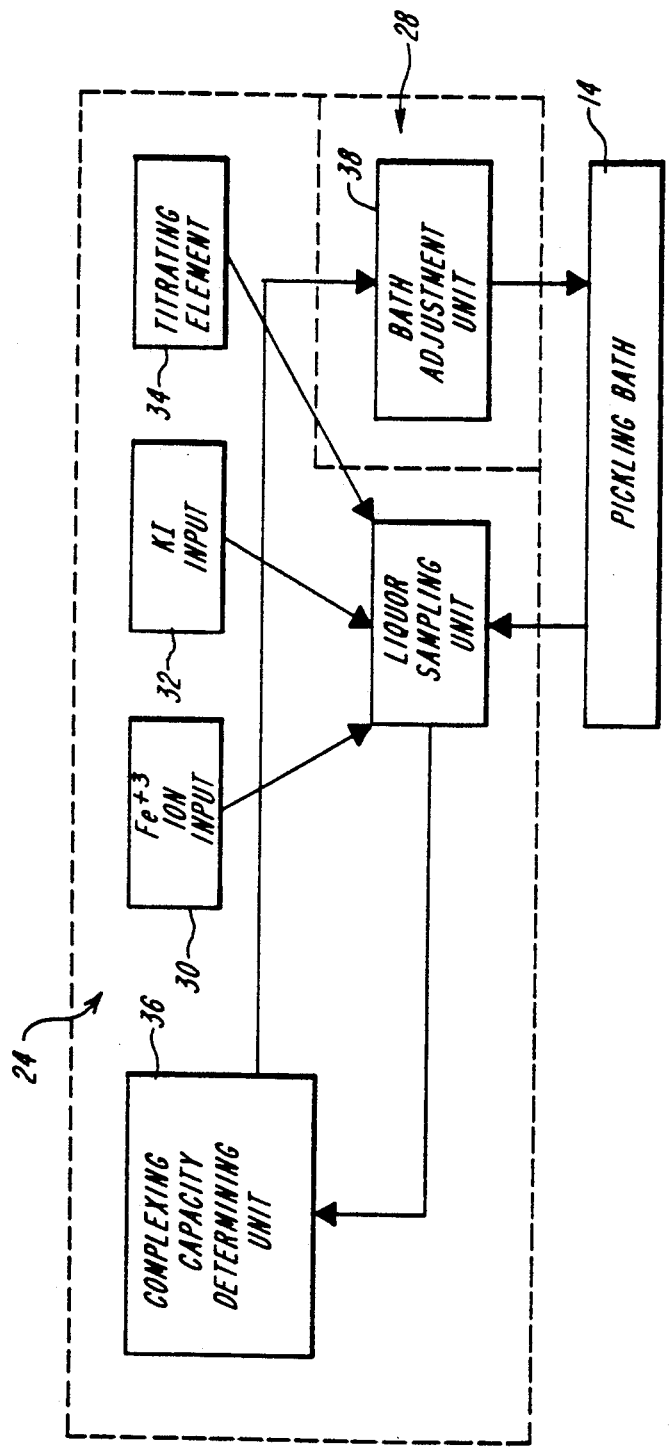
FIG. 3 is a schematic illustration of an automated system for monitoring and controlling a pickling bath according to the present invention.

FIG. 3 schematically illustrates an automated system for monitoring and controlling a pickling bath according to the present invention. A monitoring unit 24 obtains a sample of pickling liquor from a pickling bath 14. The complexing capacity of the sample is measured according to the method of the present invention. The unit 24 adds excess ferric ions through input element 30, potassium iodide reagent through input element 32, and conducts an iodometric titration through element 34. Following titration, the complexing capacity is determined through element 36. Complexing capacity data can be transmitted to a production control station 28, which may be part of or separate from monitoring unit 24. Any necessary adjustments to the pickling bath conditions are made through bath adjustment unit 38.

As noted, the method of the invention determines the effective complexing capacity (or available HF concentration) of a sample of pickling liquor. According to the method of the invention, a sample of pickling liquor is obtained from the pickling bath 18 being monitored. The sample is optionally diluted with a non-critical volume of deionized or distilled water. A known stoichiometric excess of ferric ion (Fe$^{+3}$), in a nitric acid background, is then added to the sample. The excess Fe$^{+3}$ forms complexes with the hydrogen fluoride present in the sample, such that all available fluoride is complexed to iron and an unknown quantity of uncomplexed, excess Fe$^{+3}$ remains in the sample.

Next, the uncomplexed, excess Fe$^{+3}$ is measured. Standard direct measurement techniques, such as titrations with ethylenediamine tetraacetic acid (EDTA), cannot be used for this measurement, so a back titration is utilized. Preferably, this measurement is effected in the present invention using a titration of iodine formed after addition of excess potassium iodide (KI) reagent to the sample. The uncomplexed, excess Fe$^{+3}$ and the KI reagent react as follows, in a reaction in which complexed iron does not participate:

$$2Fe^{+3} + 2I^- \rightarrow 2Fe^{+2} + I_2. \quad (1)$$

The iodometric titration which follows uses a sodium thiosulfate ($Na_2S_2O_3$) titrant. The iodine produced in reaction (1) reacts with the sodium thiosulfate titrant as follows:

$$I_2 + 2S_2O_3^{-2} = \rightarrow 2I^- + S_4O_6^{-2} \quad (2)$$

The stable, reversible Redox couple $[I^-]^2/[I_2]$ is then monitored throughout the titration addition. A milliequivalent of sodium thiosulfate required to titrate the iodine is stoichiometrically equivalent to the uncomplexed $Fe^{+3}$ present in the sample.

During the iodometric titration, voltage of the sample can be monitored using a Redox (ORP) electrode and a reference electrode to signal the equivalence point (or end point) of the reaction. The equivalence point of the reaction is that point where the proper stoichiometric amounts of the reactant and titrant are present. In the iodometric titration with sodium thiosulfate, the equivalence point occurs when one mole of iodine reacts with two moles of sodium thiosulfate.

A variety of suitable ORP and reference electrodes are known in the art. The ORP electrodes preferably are formed of non-reactive metals such as gold, platinum, palladium, iridium, rhodium, ruthenium, and osmium, that serve as media for electron transfer. The preferred materials from which the ORP electrode is made are gold and platinum. Exemplary ORP electrodes suitable for use with the resent invention include Gold ORP Half Cell (PN 118053007), available from Ingold Company of Zurich, Switzerland, and Pt ORP Half Cell (Model No. 5739182-X078B), available from Phoenix Electrodes of Houston, Tex. One skilled in the art will readily appreciate that suitable ORP sensors should not be constructed with glass or glass-filled epoxy components due to the fluoride presence in the sample.

A suitable reference electrode for use with the present invention is a flowing reference electrode having a bridge electrolyte of saturated potassium nitrate ($KNO_3$). An example of a suitable reference electrode is the Sensorex 970272 available from Sensorex of Stanton, Calif. Other suitable reference electrodes known to those skilled in the art may be used as well.

The size of the pickling liquor sample may, of course, vary depending upon the requirements of a given application. In a currently preferred embodiment, using an on-line, automated sampling and monitoring system, a 500 $\mu$l sample is used. Typically, the sample to be tested in an automated titrator such as the FPA 300 series Process Titrator is diluted with a non-critical amount of deionized or distilled water, e.g., about 20–40 ml. When a 500 $\mu$l sample diluted with 30 ml, is used, the reagents and titrants are used in volumes between about 10 and 15 ml. Where larger or smaller samples are used, the volume of reagents and titrants used will vary accordingly.

The proper concentration of reagents and titrants to be used in practicing this method is generally not critical and suitable concentration ranges will be apparent to those skilled in the art. Preferably, however, the excess $Fe^{+3}$ ions are generated through a solution of 0.1N $Fe^{+3}$, as $Fe(NO_3)_3$ in 0.1M $HNO_3$. The potassium iodide reducing agent is preferably present in a stoichiometric excess. In a preferred embodiment 0.6 M KI solution is used. The sodium thiosulfate titrant is used in a molar range of about 0.05 to 2.30M, and most preferably a 0.10M solution is used.

Figure 2:
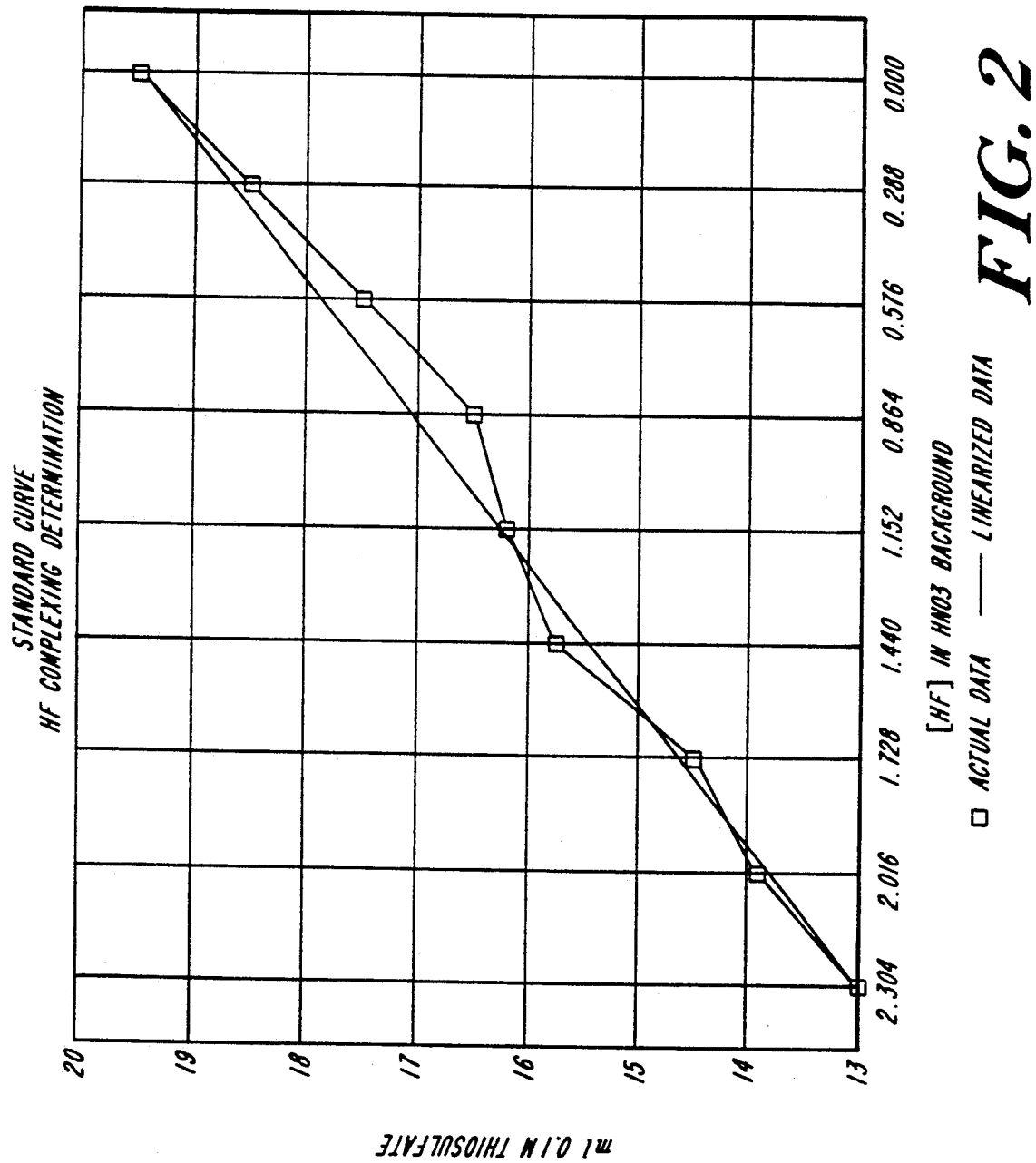
FIG. 2 is a standard curve for determining the effective complexing concentration of hydrogen fluoride, showing the efficacy of the invention, in one illustrative embodiment.

The amount of sodium thiosulfate used to reach the end point can be related to the concentration of the effective residual complexing capacity of hydrofluoric acid by comparing the results to a standard curve of the type shown in FIG. 2. The standard curve of FIG. 2, which plots milliliters of titrated 0.1M sodium thiosulfate against concentration (in molar units) of HF in an $HNO_3$ background, can be developed by known techniques using standard solutions of $HF/HNO_3$ (with no iron present) in the concentration range of interest. Pickling samples containing various amounts of ferric complexes are compared directly to this standard curve.

This method may be used in conjunction with an automated, on-line system for sampling a pickling bath, conducting titrations to determine the complexing power of the sample, and making any necessary adjustments in the pickling bath. Given the method of the invention, one skilled in the art can readily assemble the hardware and software needed to practice the method in an on-line, automated manner.

The example which follows further illustrates the invention.

EXAMPLE

An automated titrating apparatus, positioned in an industrial titrator line, gathered a 500 $\mu$l sample of pickling liquor. The sample was diluted with 30 ml of distilled water and a 14 ml solution containing 0.1N $Fe^{+3}$, as $Fe(NO_3)_3$ in 0.1M $HNO_3$, was added to the sample and mixed. After approximately 30 seconds, 10 ml of 0.6M KI was added as a reducing agent to the sample, mixed and allowed to react to yield $Fe^{+2}$ and $I_2$. Next, 0.10M sodium thiosulfate (with 0.1 g/l of $Na_2CO_3$) was added dropwise and allowed to react with the iodine in the sample. The reduction reaction of $I_2 \rightarrow 2I^-$ was monitored continuously with a gold ORP (redox) electrode and reference electrode pair attached to a potentiometer circuit. The sodium thiosulfate titrant was added until reaching an end point as determined using the potentiometer. The end point of the sample was read directly from the automated titrating apparatus in desired engineering units, having been computed from the standard points previously input.

Various modifications may be made in the invention described an claimed herein without departing from its intended scope. For example, one skilled in the art will appreciate that the quantities and concentrations of reagents may be varied to suit a given application, and that the sample size may be varied as well. Moreover, the method is adaptable for use with automated pickling liquor monitoring and control systems which may have variable hardware and software components.

What is claimed is:

1. A method of determining the iron complexing power of a liquid including hydrofluoric acid, fluoride ions, nitric acid, and complexed iron, comprising the steps of:

obtaining a test sample of the liquid;

adding a known amount of $Fe^{+3}$ to the test sample, in stoichiometric excess of the amount necessary to complex with all available fluoride ions, such that the $Fe^{+3}$ ions complex with essentially all of the available fluoride present in the sample, yielding iron-fluoride complexes and uncomplexed $Fe^{+3}$;

performing a back titration to determine the difference between the amount of $Fe^{+3}$ added to the sample and the amount of free $Fe^{+3}$ found in the sample; and calculating the complexing power of the liquid based on said difference.

2. The method of claim 1 wherein the step of performing a back titration to determine said difference is achieved by the steps of:

reacting the uncomplexed $Fe^{+3}$ with a potassium iodide reagent to yield an amount of iodine; and determining the amount of iodine by an iodometric titration.

3. The method of claim 2 wherein the iodometric titration includes the steps of adding a sodium thiosulfate titrant and monitoring the progress of the titration using a Redox electrode and a reference electrode in communication with a potentiometer circuit.

4. The method of claim 3 wherein the Redox electrode comprises a metal selected from the group consisting of gold, platinum, palladium, iridium, rhodium, ruthenium and osmium.

5. The method of claim 3 wherein the difference between the $Fe^{+3}$ added and the amount of free $Fe^{+3}$ found in the sample is inversely related to the available hydrofluoric acid concentration of the sample.

6. The method of claim 5 wherein the complexing power of the test sample is expressed in relation to the concentration of available hydrofluoric acid in the test sample.

7. The method of claim 3 wherein the liquid is a pickling liquor.

8. The method of claim 7 wherein the determination of the active hydrofluoric acid is conducted on-line, during a pickling process.

9. In an industrial pickling process comprising the step of feeding a steel material to be cleaned in the pickling process through one or more pickling baths and rinse baths, the improvement comprising the steps of periodically sampling liquid from the pickling bath;

adding a known amount of ferric ions to the sample, in stoichiometric excess of the amount necessary to complex with all available fluoride ions, such that the ferric ions complex with all available fluoride ions in the sample, leaving uncomplexed ferric ions;

reacting the uncomplexed ferric ions with a potassium iodide reagent to yield an amount of iodine;

performing an iodometric titration using a sodium thiosulfate titrant and monitoring the titration reaction until an end point is reached; and determining the complexing power of the pickling bath sample based upon the amount of sodium thiosulfate necessary to reach the end point of the titration reaction.

10. In the method of claim 9, the further step of adjusting the concentration of acids within the pickling bath based on the determined complexing power of the pickling bath sample.

11. The method of claim 9 wherein the pickling bath is sampled and analyzed approximately every fifteen minutes.

* * * * *